United States Patent
Scott et al.

(10) Patent No.: US 9,138,357 B2
(45) Date of Patent: Sep. 22, 2015

(54) THONG-STYLE SANITARY PAD AND DISPOSABLE THONG FOR SUPPORTING SAME

(76) Inventors: Hilary Brenda Scott, Kelowna (CA); Maxine Bobbie Clare Wheaton, Kelowna (CA)

(*) Notice: Subject to any disclaimer, the term of this patent is extended or adjusted under 35 U.S.C. 154(b) by 679 days.

(21) Appl. No.: 13/441,129

(22) Filed: Apr. 6, 2012

(65) Prior Publication Data
US 2012/0253304 A1 Oct. 4, 2012

Related U.S. Application Data

(63) Continuation-in-part of application No. 12/232,562, filed on Sep. 19, 2008, now abandoned.

(51) Int. Cl.
*A61F 13/15* (2006.01)
*A61F 13/472* (2006.01)
*A61F 13/475* (2006.01)

(52) U.S. Cl.
CPC ..... *A61F 13/47254* (2013.01); *A61F 13/15699* (2013.01); *A61F 13/4756* (2013.01); *A61F 13/47218* (2013.01)

(58) Field of Classification Search
CPC ............ A61F 13/472; A61F 13/47209; A61F 13/47218; A61F 13/47227; A61F 13/47236; A61F 13/47245; A61F 13/47254; A61F 13/4756; A61F 13/4758; A61F 13/475; A61F 13/4755; A61F 13/4751
USPC .......................... 604/358, 367, 385.02, 385.03
See application file for complete search history.

(56) References Cited

U.S. PATENT DOCUMENTS

| | | | |
|---|---|---|---|
| 2,206,412 A | 7/1940 | Levy | |
| 2,299,446 A | 10/1942 | White | |
| 2,636,494 A | 4/1953 | Hon | |
| 2,748,772 A | 6/1956 | Titone et al. | |

(Continued)

FOREIGN PATENT DOCUMENTS

EP  1013291 A1 * 6/2000

OTHER PUBLICATIONS

Shihui et al., "PanPad: The biodegradable sanitary pad," Singapore Management University, AY 2005/2006 Term 1, 23 pages, MGMT002: Technology and World Change.

(Continued)

*Primary Examiner* — Lynne Anderson
*Assistant Examiner* — Bradley Philips
(74) *Attorney, Agent, or Firm* — Antony C Edwards

(57) ABSTRACT

An improved sanitary pad for use in a thong-style pair of underwear to absorb and retain anticipated menstrual flow volume and at the anticipated flow rate contains a double layer of absorbent material in a waisted, water impervious flexible channel. The waisting of the channel is sized to accommodate the narrow lateral width of the thong saddle. The upright substantially flat or otherwise smooth sides of the channel guide flow entering a capture zone of the pad saddle away from the capture zone to longitudinally outer reservoir zones formed in the front and rear of the pad. In one embodiment flexible guides, which may be longitudinal rails of a flexible water-impervious substance or material, run longitudinally or substantially parallel to the sides of the channel, spaced inwardly therefrom, to assist in guiding or urging flow in and below the capture zone longitudinally towards the reservoir zones.

10 Claims, 12 Drawing Sheets

(56) References Cited

U.S. PATENT DOCUMENTS

| | | | |
|---|---|---|---|
| 3,489,149 A | | 1/1970 | Larson |
| 3,599,638 A | | 8/1971 | Rickard |
| 3,599,640 A | | 8/1971 | Larson |
| 3,613,686 A | | 10/1971 | De Woskin |
| 3,636,953 A | | 1/1972 | Benevento |
| 4,205,679 A | * | 6/1980 | Repke et al. .................. 604/366 |
| 4,430,088 A | * | 2/1984 | Karami .................... 604/385.21 |
| 4,560,381 A | | 12/1985 | Southwell |
| 4,690,681 A | | 9/1987 | Haunschild et al. |
| 4,718,898 A | * | 1/1988 | Puletti et al. .................. 604/366 |
| 4,718,902 A | | 1/1988 | Bonito |
| 4,813,950 A | | 3/1989 | Branch |
| 4,880,424 A | | 11/1989 | Rautenberg |
| 4,883,481 A | | 11/1989 | Blanchard |
| 4,940,463 A | | 7/1990 | Leathers et al. |
| 5,031,248 A | | 7/1991 | Kemper |
| 5,241,710 A | | 9/1993 | Lockhart |
| 5,325,543 A | | 7/1994 | Allen |
| 5,441,493 A | | 8/1995 | Gonzalez-Anguiano Marsel et al. |
| 5,683,373 A | | 11/1997 | Darby |
| 5,711,034 A | | 1/1998 | Cillik |
| 5,745,922 A | | 5/1998 | Rajala et al. |
| 5,827,261 A | | 10/1998 | Osborn, III et al. |
| 5,944,708 A | | 8/1999 | Philpott |
| 6,098,203 A | | 8/2000 | Rajala et al. |
| 6,193,703 B1 | * | 2/2001 | Jackson .................. 604/385.04 |
| 6,200,298 B1 | | 3/2001 | Osborn, III |
| 6,231,558 B1 | | 5/2001 | Mosley |
| 6,367,089 B2 | | 4/2002 | Van Gompel et al. |
| 6,616,649 B1 | | 9/2003 | Ismail |
| 6,673,982 B1 | | 1/2004 | Chen |
| 6,921,392 B1 | * | 7/2005 | Drevik et al. ............ 604/385.01 |
| 7,150,731 B2 | | 12/2006 | Cazzato et al. |
| 7,759,540 B2 | | 7/2010 | Litvay |
| 2006/0025745 A1 | * | 2/2006 | Toro et al. .............. 604/385.101 |

OTHER PUBLICATIONS

Stayfree, "Products for a Heavy Period", Internet article, http://www.stayfree.com/products_heavy.jsp, printed Sep. 18, 2008, 4 pages.

* cited by examiner

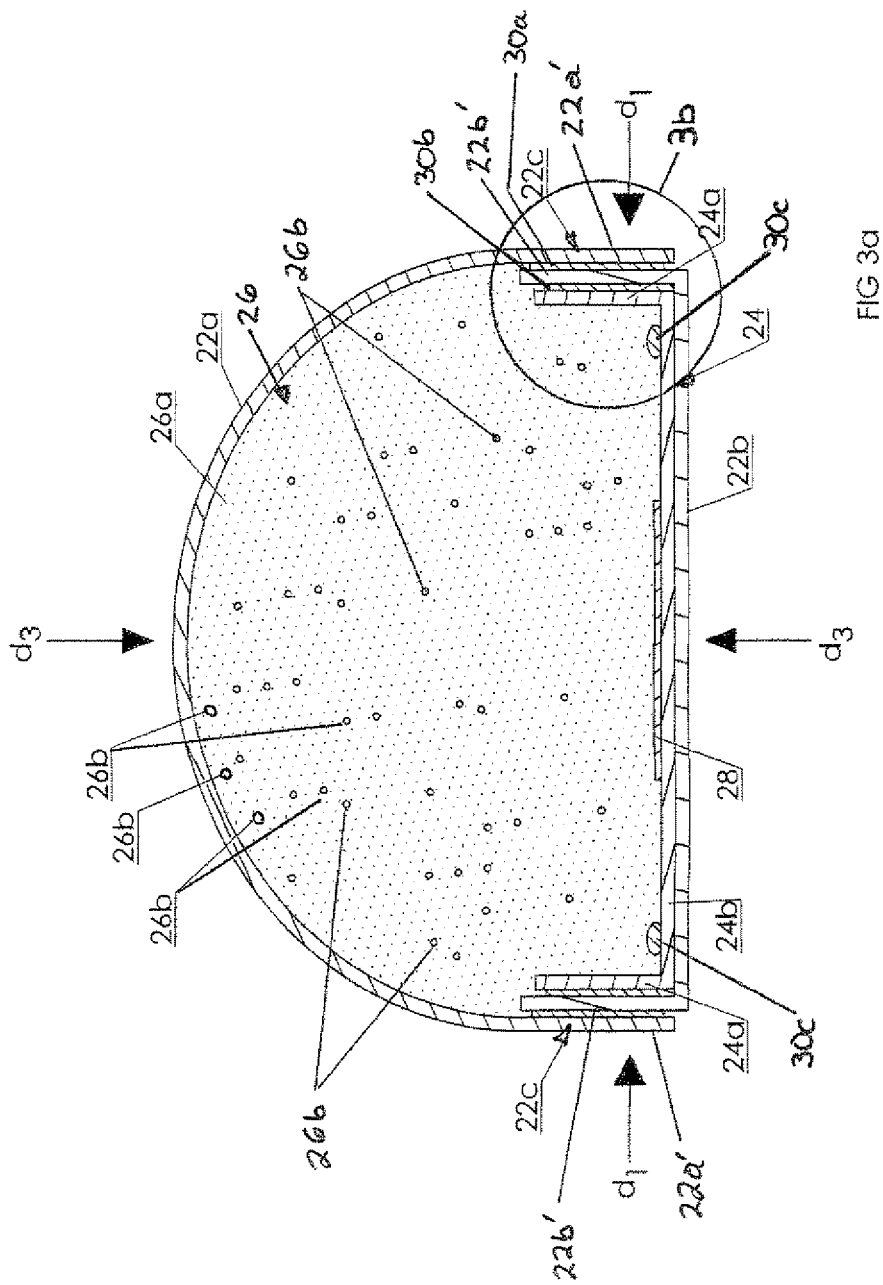

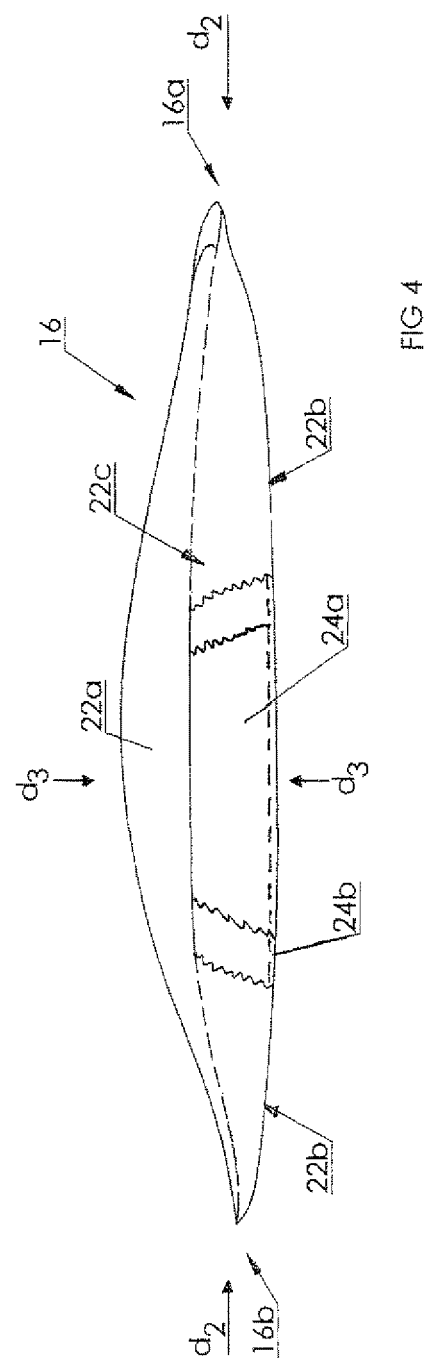

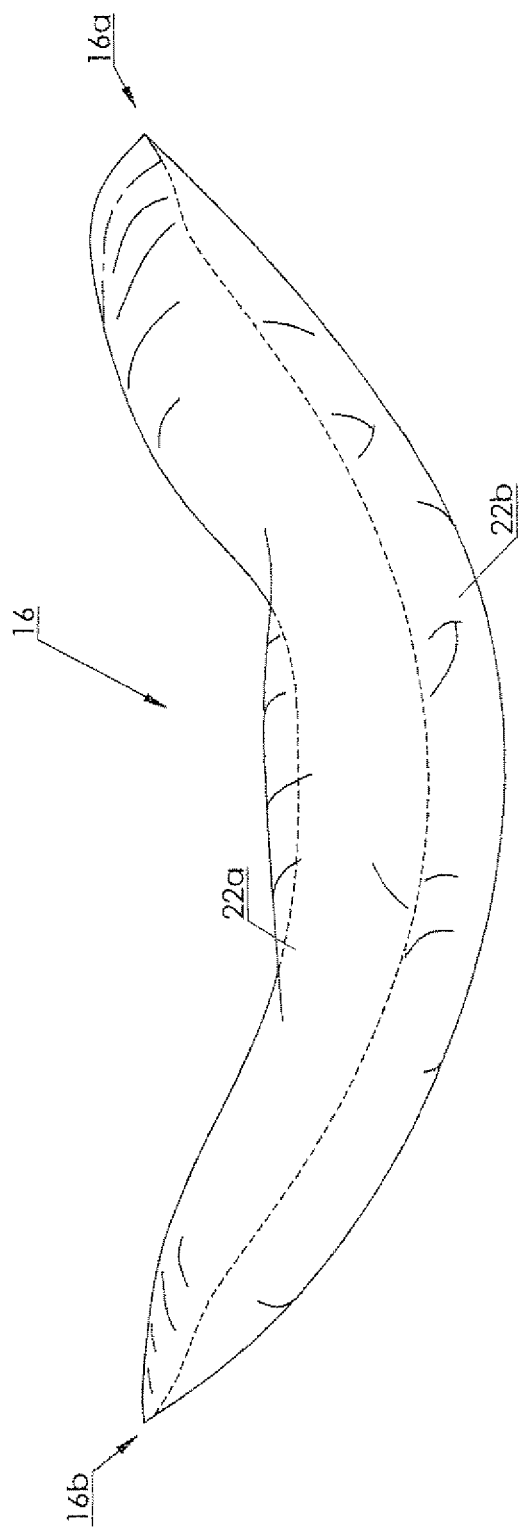

THONG-STYLE SANITARY PAD AND DISPOSABLE THONG FOR SUPPORTING SAME

CROSS REFERENCE TO RELATED APPLICATION

This application claims priority from U.S. Provisional Patent Application No. 60/960,196 filed Sep. 20, 2007, and entitled Manufacturing Unit—of All In One Panty with Sanitary Pad, and is a Continuation-in-Part from application Ser. No. 12/232,562.

FIELD OF THE INVENTION

This invention relates to the field of absorbent disposable undergarments such as sanitary pads and the like and in particular to a thong-style sanitary pad and a disposable thong incorporating same.

BACKGROUND OF THE INVENTION

As reported by Santer, Wyke and Warner in their report on their community survey and qualitative study reported in BMC Women's Health, 2007, Jun. 2; 7:8, entitled "What aspects of periods are most bothersome for women reporting heavy menstrual bleeding?", heavy menstrual bleeding is a common symptom amongst women of reproductive age and that the judgements of women reported in the survey were based on periods as a problem because of the impact of the menstrual symptoms on daily life. The impact on daily life was reported as contingent on social circumstances such as the type of paid work and other responsibilities born by the particular women. The women reportedly said that they made judgements based on what was normal for them, the degree of difficulty in containing blood loss, and the pattern of loss.

As consistently reported, excessive menstrual bleeding, commonly referred to as menorrhagia, is defined as menstrual blood loss of greater than 80 milliletres (ml), per menstrual cycle. See for example "Treatment of Menorrhagia" by Apgar, Kaufman, George-Nwogu, and Kittendorf in American Family Physician, 2007. Jun. 15; 75(12):1813-9. As reported by Engstrom, Rose, Brill, Polehill, and Lukanich in "Midwifery Care of the Women with Menorrhagia", J-nurse Midwifery, 1999, March-April; 44(2:89-105, approximately one in ten women in the United States experience menorrhagia, and although rarely life-threatening, menorrhagia can have an negative impact on women's lives and its treatment can improve the quality of life for many women with this condition.

It is applicants' understanding that a normal menstrual cycle is 21-35 days in duration with bleeding lasting an average of 5 days and a total blood flow between 25-80 ml. Reportedly it is possible to estimate the amount of bleeding by the number of tampons or sanitary pads a women uses during her period. Further applicants' understand that as a guide, a regular tampon fully soaked will hold about 5 ml of blood.

To applicants knowledge, although the prior art is replete with attempts to provide effective and convenient fluid absorbent undergarments for use in absorbing and containing a range of uterine flow volume and flow rates. In applicants' opinion, there has yet to be achieved an optimized flow retention solution which provides for containment of relatively heavy bleeding while minimising the impact of wearing such an absorbent garment on the daily life of the women users so as to reduce the women's daily problems associated with the impact of menstrual symptoms. In particular, it is often desired by women to wear garments where for example in an office work environment or in social evening wear, it is undesirable to exhibit so called panty-lines. Panty-lines are the outline depressions caused by the elasticized leg bands of panty-style underwear. Panty-lines are apparent through clingy fabric or closely conformal garments extending over the buttocks of the user, whether the garments be closely fitting dresses or the like made of light or clingy fabric, or a range of garments between shorts and pants which often provide only a smooth surface over the buttocks of the user. For such occasions, women will typically wear an undergarment commonly referred to as a thong which, in order to remove visible panty-lines, has a narrowed rear portion which extends along the depression between the buttock's cheeks. Typically a thong is asymmetric front to back where the front or crotch portion extending between the saddle (which extends under the perineum) and the waistband is larger or wider than the rear portion in terms of its surface area. The rear portion of the thong is deliberately narrowed so as to conceal the lower edges of the back or rear portion of the thong which extends from the saddle up between the depression or in fact literally between the cheeks of the buttocks. A thong may, above the narrowed portion, flare in the upward extremities of the back or rear portion so as to flare where the rear portion joins the waistband. Indeed in some thongs, as defined herein there is minimal flaring of the back or rear portion as it extends upwardly from the buttock area to the waistband.

It is applicants' experience that for women experiencing moderate to heavy flow, which as defined herein is estimated to fall within the reported definition of the norm, that is, a total blood flow between 25 ml and the statistical abnormality of 80 ml constituting menorrhagia, the available sanitary pad products are ill-suited for use when the woman user desires to wear a thong. This forces a woman to either use a tampon which she may not find effective or otherwise unsuitable for what ever reason, or to forgo the use of a thong for several or more days per menstrual cycle. In applicants' experience, the reason for the unsuitability of presently available products or those applicants are aware of the prior art, is that the designers of such products appear to assume that in order to provide maximum absorbency, that the bulk of the uterine flow is to be absorbed and mostly retained directly under the vagina and vulva. It is an object of the present invention to provide an absorbent thong-style pad for use with a thong, and in one embodiment, to provide a disposable thong having a built in thong-style pad which provides sufficient absorbency for use within the reported range of normal uterine flow rates and yet which will provide for a woman user to wear a thong while supporting such a pad. The problem thus addressed by the present invention is that of dealing with moderate to heavy menstrual flow flowing into a considerably narrowed saddle portion of the pad, hence "thong-style", which in use is under the vagina, vulva and perineum.

The narrowed portion of the saddle corresponds both to the narrowed waist of the thong underwear and to the narrowed available space between the thighs of the user. The narrowed portion of the thong-style pad according to the present invention is intended to replace the typically quite wide so-called maxi-size sanitary pads which are so wide through the saddle that they have to be bent or buckled to fit, or naturally do so during use, so that the portion intended to capture and retain flow is buckled or folded along a crease line following the crease of the perineum. It is one object of the present invention to provide a narrowed capture zone in the pad saddle which is adapted to guide flow from directly under the vagina and vulva and away to reservoir portions in the front and rear of the pad in order to avoid the flow over-filling the capture zone, and thence over-flowing causing leakage from the pad.

In the patent prior art, applicant is aware of U.S. Pat. No. 2,748,772 which issued to Titone et al for a Disposable Combined Panty and Sanitary Napkin. Titone et al disclose a panty formed of inexpensive cloth material having a pocket like crotch portion to wholly enclose a sanitary napkin. The crotch portion incorporates a piece of flexible material such as thin plastic to ensure against passage of menstrual discharge to the body portion of the panty in which the napkin is supported. Stitching is applied throughout the periphery of the inner wall, extending about the napkin and passing through the marginal area of the inner wall and through the body portion of the panty.

U.S. Pat. No. 3,599,640, which issued Aug. 17, 1971, to Larson for A Disposable Undergarment with Absorption Pad, discloses a disposable waist supported garment including an integral absorbent crotch pad. The components parts of the garment are heat formed and heat sealed. The edges are crimped to form a ribbed effect which is stretchable to sit against the body of the user. The pad is permanently secured to the crotch of the undergarment by a suitable adhesive or by heat sealing, etcetera.

U.S. Pat. No. 4,560,381, which issued Dec. 24, 1985, to Southwell for A Disposable Panty for Menstrual Wear discloses a woman's panty for removably carrying a feminine napkin. It is taught to include a lightweight disposable biodegradable mesh-like outer panty shell to which is affixed or is contiguous with a relatively thick inner layer of absorbent material disposed above the inner surface of the lower body portion of the panty. An elongated, nearly rectangular depression or indentation having oval end portions is included or formed in the relatively thick layer for carrying, lining or positioning a feminine napkin.

U.S. Pat. No. 4,690,681, which issued Sep. 1, 1987, to Haunsehild et al for A Disposable Leak Proof Catamenial Device discloses a panty-like garment containing an integral menstrual pad. The absorbent pad is taught to extend from the crotch region up in both the back and the front to a point which is higher than normal menstrual pads. It is disclosed that the pad extends at least to the area where the crack between the gluteus maximus ends. It is further taught that an impervious member outside of the absorbent pad is greater in area than the absorbent pad. It is also disclosed that the garment may be constructed by placing an absorbent pad on an impervious backing placing a permeable member over the pad and sealing the impervious member and the permeable member together by ultrasonic's where they contact each other outside of the absorbent member, the composite absorbent structure then being bonded to the crotch section of the panty.

U.S. Pat. No. 4,940,463 which issued Jul. 10, 1990, to Leathers et al for A Disposable Combined Panty with Sanitary Napkin discloses a disposable panty having a tubular body portion with an hour-glass configuration to provide an intermediate crotch portion. A sanitary napkin is disposed within the crotch portion. The sanitary napkin includes a frame member provided with absorbent balls disposed in the opening of the frame member to increase the absorption of the menstrual discharge. A flexible liquid impervious material is disposed between the outer layer of the body portion and the sanitary napkin.

U.S. Pat. No. 5,441,493, which issued Aug. 15, 1995, to Gonzalez-Anguiano Marsel et al for Disposal Panties discloses using a sanitary napkin member which is positioned over a longitudinal under-crotch portion of the under pant body of a disposable pair of underpants. The sanitary napkin is only secured to the under pant body along the inner surface thereof and only along the rear and longitudinal edges of the sanitary napkin. An increased density material is provided within the under-pant body at the rear end portion thereof coextensive with the longitudinal under-crotch portion to resist tearing of the rear end portion during flexing of the underpants. The sanitary napkin includes a mini sanitary towel which is attached to the perineum area of the panties by stitching. The central area of the towel is thicker than the front and rear areas.

U.S. Pat. No. 5,745,922, which issued May 5, 1998, to Rajala et al for a Disposable Garment and Related Manufacturing Equipment and Methods, discloses a disposable garment for holding a primary absorbent sanitary pad. Backup protection is provided to control egress for fluids around or through the primary sanitary pad. A secondary absorbent is positioned in the crotch area and extending into the body of the disposable garment to trap leakage from the garment and to trap leakage from the primary absorbent. Elastics extend along the leg openings to form puckers about the leg openings at the edges thereof. The width of the crotch portion is wide enough to accommodate laying the primary absorbent without having the primary absorbent obstruct the crotch elastics. This is taught to allow the crotch elastics to contract and draw up the sides of the crotch about the primary absorbent to contain leakage from the primary absorbent. The width of the crotch portion between the elastics is taught to be not so wide as to seem bulky or uncomfortable, a suitable width being given of at least about 2.75 inches between the crotch elastics, the crotch elastics being taught to be approximately ⅓ to ½ of an inch wide. It is disclosed that the overall width of the crotch portion should be at least about 4 inches. It is taught that preferably the width of the secondary absorbent is equivalent to the overall width of the crotch portion and that the secondary absorbent should have a total capacity of ½ the capacity of the primary absorbent. It is taught that the position and shape of the leg openings are important to avoid tightness in the crotch and groin area and to obtain adequate buttocks coverage.

U.S. Pat. No. 6,231,558, issued May 15, 2001, to Mosley for A Sanitary Undergarment discloses an undergarment which is disposable and which contains a middle region having resiliently elastic material adapted for constricting the middle region around a wearer. A lower region includes a substantially water impermeable material for preventing the passage of menstrual fluids. The lower region is beneath the middle region and includes a crotch region having a primary absorbent pad, and a secondary absorbent pad on the primary absorbent pad. Resiliently elastic leg bands are provided around the outer perimeter of the leg openings. Absorbing strips extend along a semi-circular lower portion of a circumference of the adjacent associated leg opening to absorb fluid in the lower region that may accumulate near the leg openings.

U.S. Pat. No. 6,193,703, issued Feb. 27, 2001, to Jackson for an Adjustable Scroll Absorbent Article and Method discloses providing side leakage protection and positioning guidance for an undergarment. A liquid-impermeable baffle provides the side leakage protection.

U.S. Pat. No. 5,683,373, issued Nov. 4, 1997, to Darby for a Sanitary Napkin Shaped for Use with a Thong Garment discloses a napkin which is generally v-shaped so that the vertex of the "V" can be positioned below the vagina of the wearer. It is designed so that the narrowest tip portion of the napkin terminates just beyond the lower most portion of the vagina, so as to terminate shorter than usual designs. There is no back portion. The top end of the napkin is bulb shaped.

U.S. Pat. No. 7,759,540, issued Jul. 20, 2010, and published Jan. 29, 2004, under publication no. US2004/0019338, to Litvay et al for Absorbent Articles Containing Absorbent Cores having Zoned Absorbency and Methods of Making Same, discloses the use of specific placement of adhesives or specific lack of adhesives to provide zoned absorbency in the absorbent core of an absorbent article. Litvay teaches the use of adhesive (295) in a number of different embodiments to cause more tow fibers (288) and super-absorbent polymer (SAP 286) to adhere in regions where the adhesive is applied thereby providing greater zones of absorbency in specific areas on the absorbent laminate core. It is taught as preferred that the adhesive is applied in a spiral manner, and more particularly to provide a curtain coat of the adhesive intermittently to the upper and lower layers, and not to apply the adhesive in a spiral pattern in the areas where zoning of the SAP is desired. It is disclosed that by not employing the adhesive to either the top or bottom layers of the absorbent laminate core, increased concentration of SAP can be provided in the areas of the cores where it is need most, the example being given of the lowest portion of the core as being beneficial since most liquids tend to migrate to the lowest gravitational point of the core. The example is also given of enhanced absorbency near the lateral edges of the core (FIG. 3).

SUMMARY OF THE INVENTION

In summary, the thong-style sanitary pad according to one aspect of the present invention includes a flexible fluid impervious lower layer, a flexible, fluid absorbent core mounted on the lower layer, a flexible, porous upper layer mounted atop the fluid absorbent core, wherein the fluid impervious lower layer is formed as a fluid diverting and containment channel.

The lower layer, when laid flat, has an elongate substantially planar fluid impervious base extending longitudinally between opposite front and rear ends thereof and extending laterally between opposite first and second side edges thereof. The first and second side edges are substantially mirror images of each other. Each side edge has a concave outline in plan form between the front and rear ends so as to define a waist along a mid-portion of the base between forward and rearward portions of the base adjacent the front and rear ends of the base respectively.

The lower layer has substantially smooth side walls extending upwardly from the base along the first and second side edges corresponding to at least the mid-portion of the base. Advantageously the side walls extend along substantially the entire length of the side edges of the base of the lower layer.

The upper layer has first and second side edges which are mounted to corresponding the first and second side edges of the lower layer. The upper layer also has front and rear ends which are mounted to corresponding the front and rear ends of the lower layer so as to encase the fluid absorbent core between the upper layer, the base and the side walls of the lower layer, and wherein the fluid absorbent core extends substantially from the front ends to the rear ends of the upper and lower layers. Advantageously, the fluid absorbent core extends substantially from one side edge to the other side edge of the upper and lower layers.

In a preferred embodiment the waist is sized to snugly fit in use of the pad, without substantial folding about a longitudinal axis of the pad of the mid-portion of the lower layer and corresponding mid-portions of the core and the upper layer, whereby a user so wearing the pad under a perineum area of the user will fit the waist between a saddle portion of a thong being worn by the user and the user's perineum without the substantial buckling of the pad.

In the preferred embodiment the sidewalls extend upwardly substantially orthogonally from the base when the base is laid flat. The height of the sidewalls will depend on how thick the pad is. A thinner pad, for light flow days, would have lower sidewalls. Conversely, a thicker pad, for heavy flow days, would have higher sidewalls.

The present invention may also include a disposable thong portion for supporting the upper layer of the pad against the perineum and vulva of the user, and so as to position the mid-portion of the pad adjacent the vulva of the user.

A flexible lower cover layer having circumferential edges therearound may be mounted under the lower layer. The circumferential edges of the lower cover layer may be mounted to the edges of the upper layer along an upwardly oriented boundary seam. The seam may extend along the sidewalls so as to support the sidewalls in their upward substantially orthogonal orientation relative to the base of the lower layer.

The pad may also advantageously include a longitudinally extending flexible pair of flow guiding rails mounted to an upper surface of the base. As used herein, the term rails is intended to include resilient low-rise, elongate flow-guiding structures that are much narrower than they are long. For example such flow guide structures may be elongate beads, ridges, rails, strips, slats, herein collectively referred to a flow guiding rails. Each rail of the pair of flow guiding rails are low-rise, that is, of a low height and positioned adjacent a corresponding sidewall. The height of the flow guiding rails may be in the order of 0.5-3.5 millimeters, or more preferrably 1-3 millimeters, or for example approximately one twentieth (5%) to one tenth (10%) the height of the sidewall. The flow guiding rails may be adjacent or snugly adjacent or in contact with the sidewalls along an upward fold line wherealong the sidewalls bend upwardly from the base or floor of the pad. The pair of flow guiding rails may be a pair of resilient beads or strips. The beads or strips may be beads or strips of adhesive. The core may rest on the adhesive beads or strips.

In certain embodiments the base or floor and sidewalls of the lower layer are formed from a single sheet of water-impervious material or fabric. The resilient rail, which may be of adhesive or of other water insoluble resilient material, may be applied in liquid or semi-liquid form, or as laid-on strips which are subsequently heated, along the sidewall fold onto the base or floor so as to form a flow barrier which extends longitudinally along the base or floor.

The pair of low rails may form opposite sides of a continuous flexible rail extending substantially continuously around a circumferential edge of the base.

Advantageously, the waist has a lateral dimension and a corresponding vertical dimension and wherein a ratio of the vertical dimension to the lateral dimension is substantially in the range of a ratio of ½:1 to a ratio of 1:1.

The present invention also includes the corresponding method for making the pad according to this summary.

BRIEF DESCRIPTION OF THE DRAWINGS

FIG. 1b is, in rear perspective view, the thong and pad of FIG. 1a.

FIG. 1c is, in front perspective view, the thong and pad of FIG. 1a.

FIG. 2a is, in partially cut-away front elevation view, the thong and pad of FIG. 1a.

FIG. 3a is a cross-sectional view along line 3a-3a in FIG. 1a.

FIG. 3b is an enlarged view of a portion of FIG. 3a.

FIG. 4 is, in partially cut-away side elevation view, the pad of FIG. 1a.

FIG. 5 is, in side perspective view, the pad of FIG. 1b.

FIG. 6 is a sectional view along line 6-6 in FIG. 1a.

DETAILED DESCRIPTION OF EMBODIMENTS OF THE INVENTION

Figure 1A:
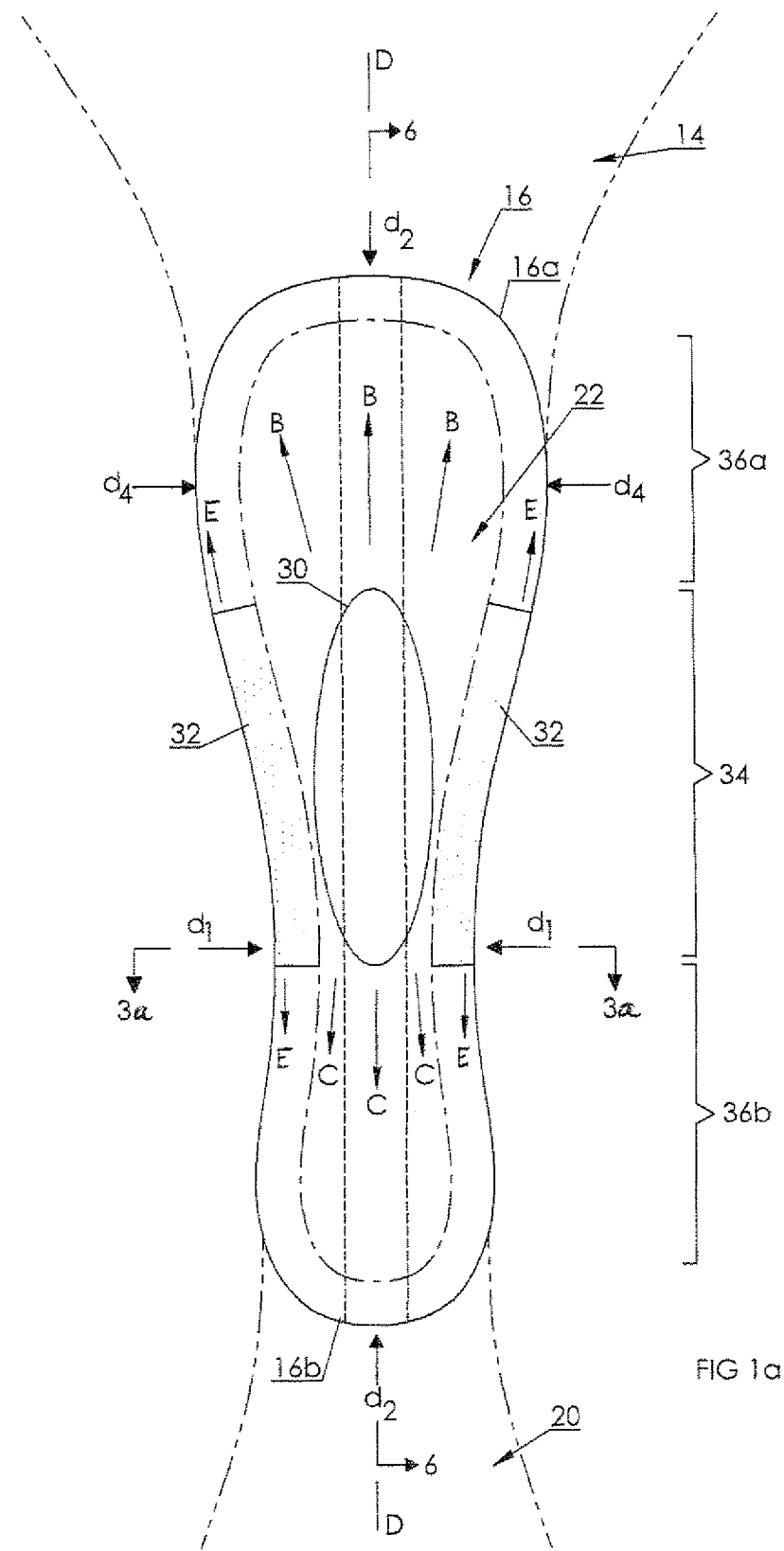
FIG. 1a is, in plan view, a thong-style sanitary pad of the thong-style sanitary pad and thong for supporting same according to the present invention.

The present invention is an improved sanitary pad which is adapted for use in a thong-style pair of underwear and in one embodiment includes a disposable pair of thong-style underwear which have the thong-style sanitary pad according to the present invention built in to the underwear's saddle. To absorb and retain the anticipated menstrual flow volume and at the anticipated flow rate, a double layer of absorbent material is contained in a waisted, water impervious flexible channel within the pad where the waisting of the channel is sized to accommodate the narrow lateral width of the thong saddle, and where the upright substantially flat sides of the channel guide flow entering a capture zone of the pad saddle away from the capture zone to longitudinally outer reservoir zones formed in the front and rear of the pad. In one embodiment low-rise flexible guides or rails, which may be longitudinal ridges, rails, beads, strips, slats of a flexible water-impervious substance or material (collectively herein referred to as flow guiding rails), run substantially parallel and adjacent to the sides of the channel, to assist in guiding or urging flow in and below the capture zone along towards the reservoir zones. In one embodiment the low-rise rails or beads are inset from the fold-line between the pad floor and the sidewalls, and in another embodiment they are along the fold-line.

Thus as seen in the accompanying figures wherein like reference numerals in the various figures depict corresponding parts in each view, thong 10 includes a waistband 12 which may be fastened around the waist of a user by conventional fasteners including for example hook and loop fasteners 12a. Of course other fasteners will do, or alternatively, the waistband may be elasticised or otherwise not require fasteners, although fasteners are preferred so that the thong may be removed and replaced without the need for the wearer to remove her shorts, pants or other legged garment. Further, it is understood that in FIG. 1 and the other figures depicting thong 10, although the thong is depicted for clarity by way of simplified line drawings, it is understood that the present invention is intended to include thongs having fanciful, decorative, designs or external finishes including feminine finishes that may include lace, ruffles or adornments typically found in commercially available underwear.

Further, applicants' do not intend that the exact dimensional representations of the thong per se are to be limiting as it is specifically intended in the present invention to include the many shapes and forms of what is referred to herein as thong-style underwear which have the common characteristic that a thin strip of material runs along the centre of the garment, upwardly and rearwardly from a narrow saddle which sits under the wearers crotch (vulva and perineum), so that the thin strip of material sits between the wearer's buttock cheeks so as to connect the saddle to the waistband. As used herein, it is intended to include within the reference to thong-style underwear thongs as small as so-called g-strings or their equivalent and, in increasing material surface area, up to and including styles more closely reassembling the panty portion of a so-called bikini-style or a so-called "booty short" or "boy short". Again, the common element of such styled underwear, is that the saddle extending under the crotch of the wearer is necessarily narrow as it waists into the junction with the rear rising portion of the buttock area of the underwear. For example, the narrowest waisted dimension d1 in saddle 18 may be in the order of 3 centimetre (cm) or less in lateral dimension, and in preferred embodiments may have a d1 dimension of 4.5 cm and a d3 dimension of 3.5 cm, although these are not intended to be limiting as thinner, smaller lighter-flow-days pads will also work. The preferred ratios of dimensions d3:d1 may be in the range of 0.66 (d3/d1), although it is intended that the scope of the present invention extend to a ratio of d3:d1 of substantially one, i.e., where d3 is substantially equal to d1.

Thus thong 10 includes a front v-shaped portion 14 which extends downwardly from waistband 12 to where thong pad 16 overlays or is built in to form part of saddle 18. The forward end 16a of thong pad 16 extends upwardly from saddle 18 so as to overlay onto or be adjacent to front portion 14. The rearward end 16b of thong pad 16 is oppositely disposed to forward end 16a and overlaps onto or is adjacent to the rearwardly and upwardly extending rear portion or thong strip 20.

Thong pad 16 has a porous or otherwise fluid-pervious sleeve-like housing in which the absorbent material and fluid impervious channel as better described below is encased. The sleeve may be of fabric and may be a continuous fabric sleeve or, as depicted, fabric sleeve 22 may be comprised of an upper layer 22a mounted to a lower layer 22b for example along seams 22c. Seams 22c may be abutting seams, or may be overlapped seams where either, as illustrated, the edges 22a' of upper layer 22a overlay the corresponding edges 22b' of lower layer 22b, or conversely where the edges 22b' of lower layer 22b overlay the corresponding edges 22a' of upper layer 22a. Where sleeve 22 is comprised of upper and lower layers, is intended that edges of the layers be mounted one to the other without the need for stitching or other mounting means which perforate the corresponding inner fluid impervious channel 24. Thus for example seams 22c could be formed by adhesives or by heat or chemical welding. Thus as seen for example in the sectional view of FIG. 3a, the longitudinally extending substantially flat side walls or gussets 24a of channel 24 are folded upwardly from the longitudinal side edges of the fluid impervious floor or base 24b of channel 24, when thong pad 16 is laid flat. Side walls 24a extend upwardly generally orthogonally to floor 24b. In use the forward end 16a and rearward end 16b of the pad will be uplifted as the pad is bowed so as to be concave in side profile as seen in FIG. 5.

The primary absorbent material 26 may be short-fibre absorbent stuffing 26a such as for example chopped cotton or so called "cotton wool". It is known in the prior art to include in such absorbent filler, distributed therethrough, fluid-absorbent micro-spheres 26b, being very small balls of absorbent gel interspersed apparently to applicants' observation somewhat evenly throughout the cotton. The primary absorbent material 26 is conventional and is found in commercially available absorbent sanitary pads such as those sold by the Johnson & Johnson Company of Langhorne, Pa., USA, under the trade-mark Stayfree™ maxi-pad.

A secondary fluid absorbent layer 28 may also be provided. Layer 28 may take the form, although it is not intended to be limiting, of a commercially available strip or bead of fluid absorbent gel running longitudinally along all or part of the upper surface of floor 24b of the fluid impervious layer 24. Such a strip is apparently presently commercially available as it is used in the aforementioned Maxi-pads. Thus, fluid absorbent layer 28 may be a strip running the longitudinal length d2 of thong pad 16. Length d2 may for example be in the order of 18-20 cm, although this is not intended to be limiting.

Figure 6:
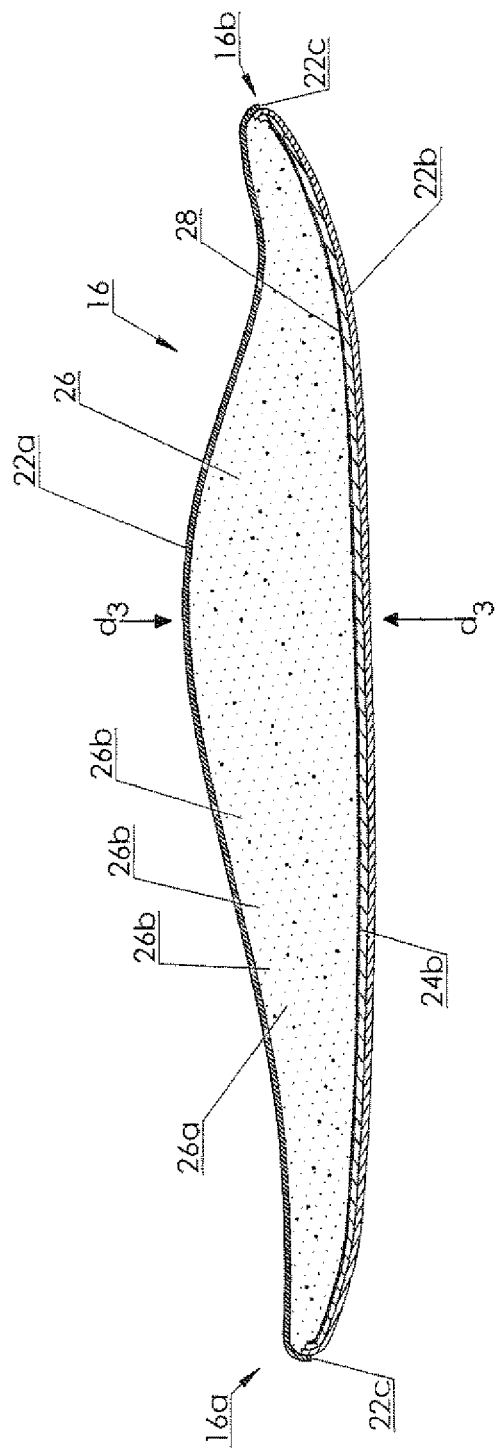
Figure 7:
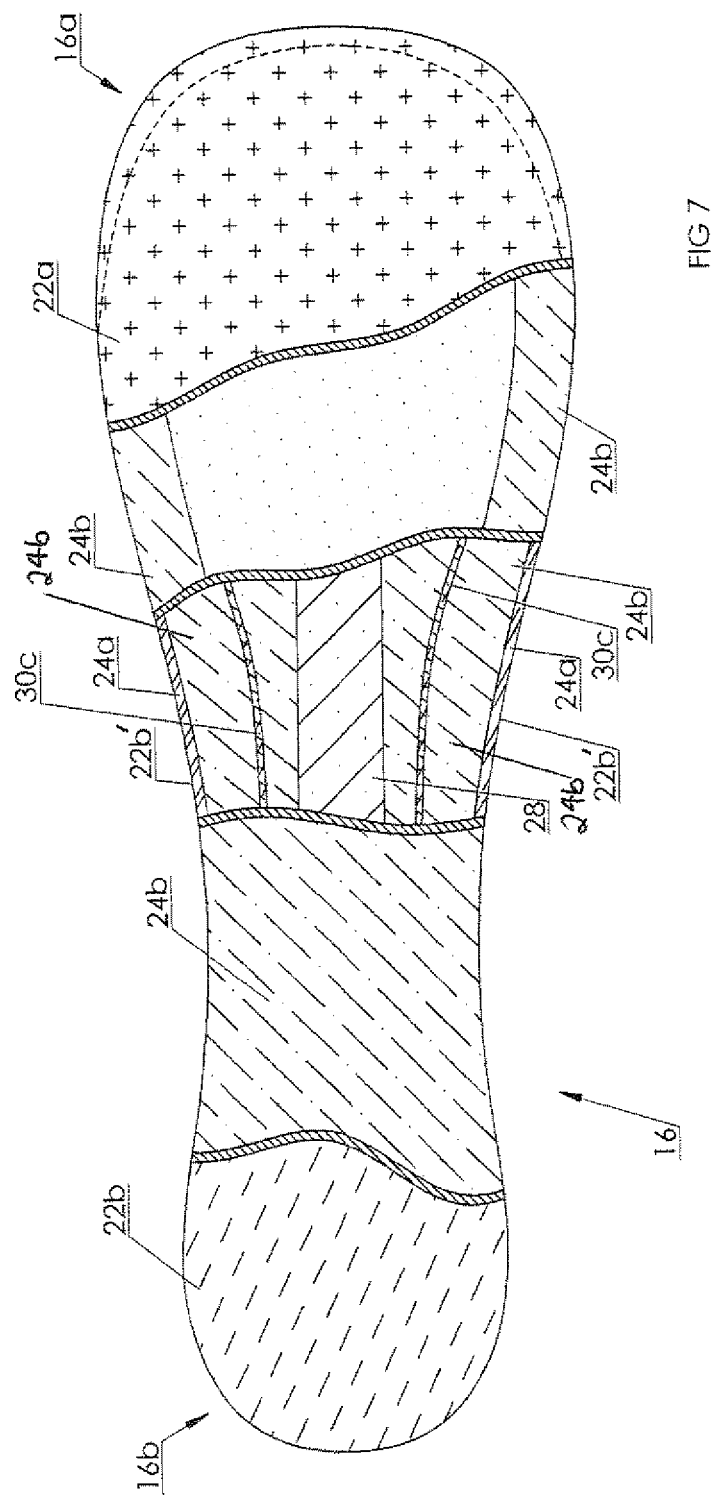
FIG. 7 is, in plan view, the pad of FIG. 1a cut-away to show five layers in the pad's construction.
Figure 8:
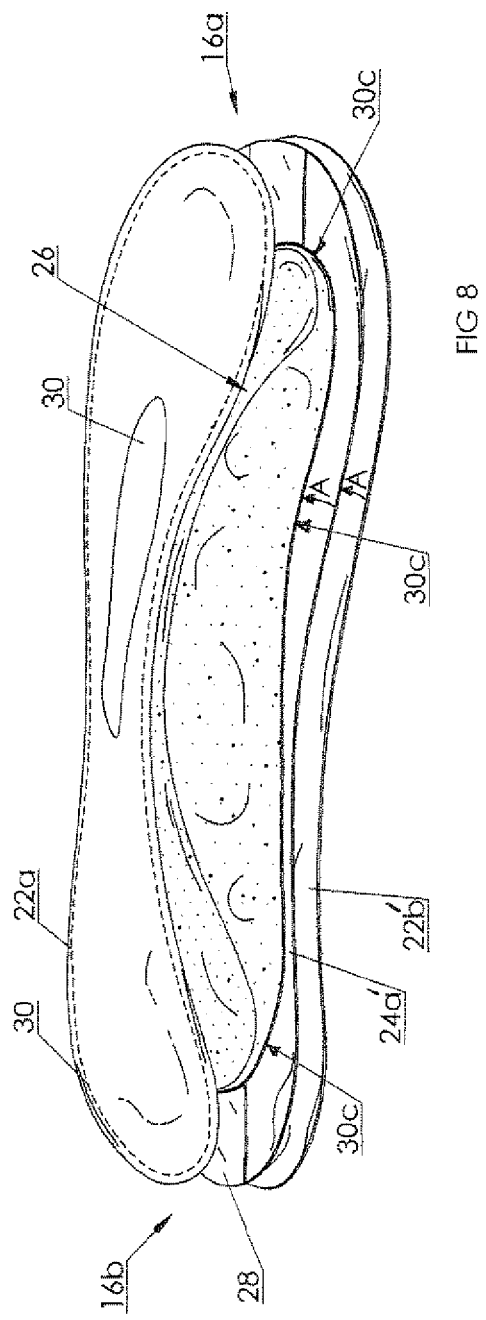
FIG. 8 is, in partially exploded side perspective view, the pad of FIG. 4.

Seen in the longitudinal cross section then of FIG. 6, primary absorbent material 26 reaches a maximum vertical thickness in direction d3 substantially where the waist distance d1 is a minimum, although it is intended that a significant, if not equal, vertical thickness continue forward of the waist at d1 so as to provide such significant thickness under initial flow entry area 30, which is intended as that area under the vagina opening of the user. Height d3 may for example as mentioned above be in the order of 4 cm, although pads of lesser height will work and are intended to fall within the scope of the present invention. As seen in the partially exploded view of FIG. 8, the outer edges 22b' of lower layer 22b and the corresponding outer edges 24a' of fluid impervious layer 24 may be folded up in direction A along the length of the longitudinal edges thereof so as to form, when generally vertical, side walls or gussets 24a adjacent the upturned edges 22b' of lower layer 22b. Once the edges are turned up so as to form side walls 24a, the upper layer 22a may be pressed down onto layer 26 so as to encapsulate the absorbent layers 26 and 28 sandwiched between upper layer 22a and fluid impervious layer 24. The edges 22a' and 22b' of upper and lower layers 22a and 22b respectively are then joined together along seam 22c. In one embodiment, a bead or strip of adhesive 30a is used to adhere the edges 22a' of upper layer 22a to the edges 22b' of lower layer 22b along seam 22c. A further bead or strip of adhesive 30b may be used to adhere side walls 24a to edges 22b'.

In one embodiment, which is not intended to be limiting, a further resilient or flexible flow guiding rail, for example a bead of resilient, flexible adhesive 30c, is applied along each longitudinal edge of floor 24b of layer 24, so as to run the length of at least a mid-portion of pad 16 inset from side walls 24a. Flow guiding rails such as beads 30c may run in parallel to each other, or as illustrated, in parallel with the waist contour or curvature of side walls 24a as the side walls follow the contour of the waist, or some variation of those two patterns so long as the flow guiding rails are spaced apart laterally and extend lengthwise or longitudinally at least the length of the mid-portion of the pad. It is thought that, even though of minimal height, flow guiding rails such as beads 30c or other low-rise longitudinal ridges, strips, etc assist in guiding the fluid flow longitudinally away from flow entry area 30, although applicants do not wish to be held to any particular theory of the applicable fluid flow mechanics. In a further embodiment, rails such as bead 30c continues continuously around the perimeter of floor 24b.

Applicant's have discovered that merely a pair of rails or beads spaced inwardly from substantially vertical side walls, which are also fluid-impervious, serves to transport a relatively high volume of liquid away from the target area by what applicants believe is re-direction of the lateral flow into longitudinal flow thereby sending the fluid into the forward and rearward reservoir areas, and in particular into the forward reservoir which may, in a thong-style undergarment, be made larger in area due to the larger area of the undergarment covering the pubis. If a larger forward fluid absorbent area is provided such as by Darby, without a means to direct the flow longitudinally from the target area into the forward reservoir area, the provision of a reservoir area which merely relies on natural wicking of the absorbent material, will not in applicants belief avoid over-saturation, and hence a likelihood of leaking, of the waisted portion of the absorbent core due to lateral flow.

Figure 3B:
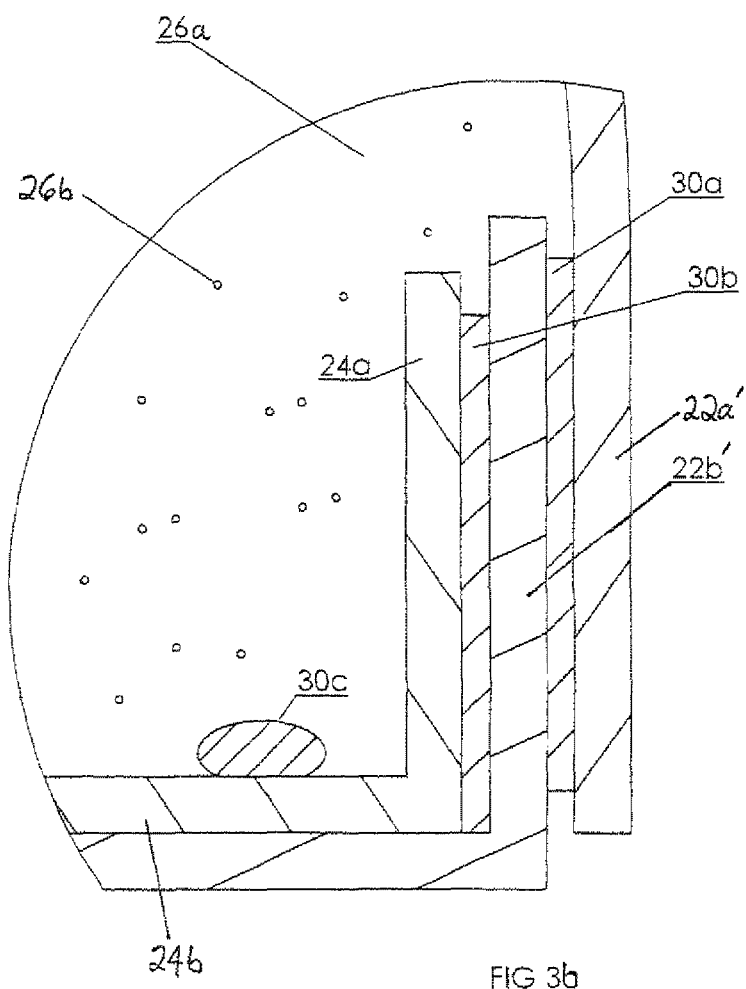
Figure 3C:
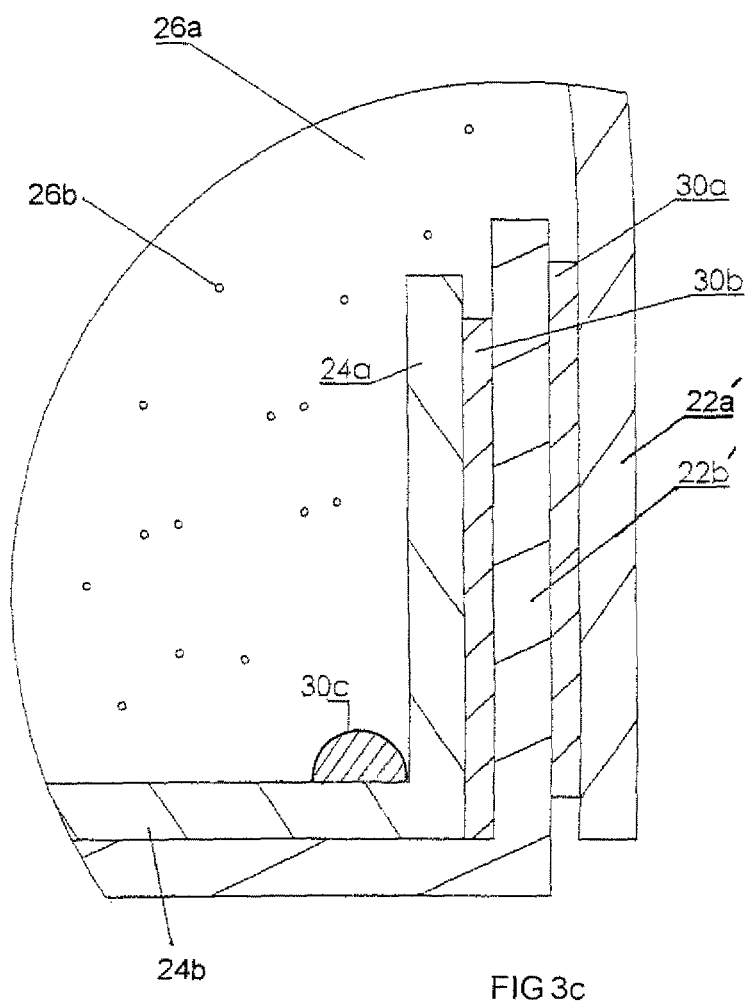
FIG. 3c is, in an enlarged view of FIG. 3b, an alternative embodiment wherein the resilient bead or rail is along the sidewall fold-line.

As used herein, the term flow guiding rail, such as "beads", is intended to confer the relative proportions between the height of the beads 30e and the height of the side wall 24a and the relative proportions between the height of the beads 30e and the height of the absorbent core 26. In the latter, the height of the beads are, as illustrated in FIGS. 3a and 3b, are a small percentage of the height of the core, and in the former, not a significant percentage of the height of the side walls for example approximately 5-10% the height of the sidewall 24a. The core extends over so as to rest on the flow guiding rails, and is intended to infer a height restriction on the flow guiding rails. If the flow guiding rails such as beads 30c are too high or too thick, or otherwise have too much mass, then the pad will lose its flexibility and become more uncomfortable to wear even if made form very flexible or very resilient material.

If the rails such as beads 30c are too insignificant then little inhibiting of the lateral flow and little redirection of the lateral flow into longitudinal flow will be obtained. Thus for example the flow guiding rails such as beads 30c may be advantageously substantially in the range of 0.5-3.5 millimeters, or in one embodiment in the range of 1-3 millimeters in height above the floor 24b of the fluid impervious layer 24.

A further strip of adhesive (not shown) may be provided along the underside of the lower-most layer of the pad. This strip of adhesive allows the pad to be removably mounted in the saddle of a conventional thong-style pair of under wear. Such a strip of adhesive is a conventional form for mounting sanitary pads in underwear. So-called "wings" (not shown) may also be provided to accomplish the same removable mounting. Such wings are typically fabric or other flexible absorbent material which extend laterally outwardly of the normal edge of the pad, i.e. the edge which lies within the saddle of the underwear, and which are folded under the saddle of the underwear so as to bear an adhesive on the wings against the fabric of the underwear to thereby clamp the saddle between the folded-under wings and the pad atop the saddle.

In experiments with pad prototypes incorporating the present invention, the upper and lower layers of 22a and 22b were of non-woven fabric and in particular fusible interfacing as used in sewing. The contents of a conventional maxi-pad were used as the material for absorbent layer 26. A maxi-pad was cut open and the absorbent material, which appeared to be cotton wool which included dispersed gel-like small absorbent balls, was weighed at 0.2 oz. A plastic backing layer 24 was over laid onto the bottom layer 22b of interfacing. A bead of glue 30b secured the backing layer to the bottom layer. A further bead of glue 30c was applied around, and inset from, the edge of the backing layer and the absorbent cotton wool material 26 then pressed down onto the backing layer and down onto the bead of glue on the backing layer. A further bead of glue 30a was applied around the perimeter of the edge 22b' of the bottom layer of interfacing 22b and the upper layer of interfacing 22a was over laid and edges 22a' pressed down onto and around the edges 22b' of the bottom layer.

Second and third prototypes were assembled the same way using, respectively, 0.25 oz of absorbent material and 0.3 oz of absorbent material between the upper and lower layers of interfacing. All three prototypes had the plastic bottom layer laid on top of the lower layer of interfacing so as to provide a fluid impervious barrier between the lower layer of interfacing and the cotton wool and gel-balls mixture. The edges of the interfacing were cut with a wider dimension to allow for the folding over of the edges, one on top of the other to form a pair of side walls (along seam 22c) containing both the absorbent cotton wool 26 and the fluid impervious backing layer or film, which was also cut so as to allow for the sides of the film to be folded upwardly to be adjacent seam 22c so as to encase the corresponding sides of the absorbent cotton wool. The side walls did not extend upwardly a very great distance; only a fraction, for example approximately one cm, of the total maximum vertical height of the absorbent material at its thickest.

For testing of the prototypes, a hollow mannequin (not shown) was used. The crotch of the mannequin was perforated with small holes. Commencing with the prototype containing 0.2 oz of absorbent material, and with the prototype thong pad built into the saddle of a thong-style pair of underwear also fashioned from interfacing, the first prototype was mounted onto the mannequin so as to position the thong pad underneath the perforated crotch area of the mannequin. With the thong pad held in place by the waistband, coloured water was slowly poured onto the interior side of the perforated plastic crotch of the hollow mannequin. The water was slowly poured in 20 cc increments. The procedure was repeated until 100 cc of coloured water had been poured into the perforated crotch of the mannequin and had passed through the perforated crotch into the thong pad mounted there under. No leaks from this pad were observed. The tested were repeated with the prototype containing 0.25 oz of cotton wool and with the prototype containing 0.3 oz of cotton wool. That is, the testing protocol was followed using increments of 20 cc of coloured water and repeated the pouring 20 cc of coloured water into the perforated crotch of the mannequin so that it flowed into the thong pad until 80 cc had been allowed to penetrate in slowly added 20 cc increments into both the second and the third prototypes. Again, no leakage from either the second or third prototype was observed. Further slowly added 20 cc increments of coloured water were added. At 120 cc again no leakage was noted. Leakage was noted at 150 cc.

Figure 1B:
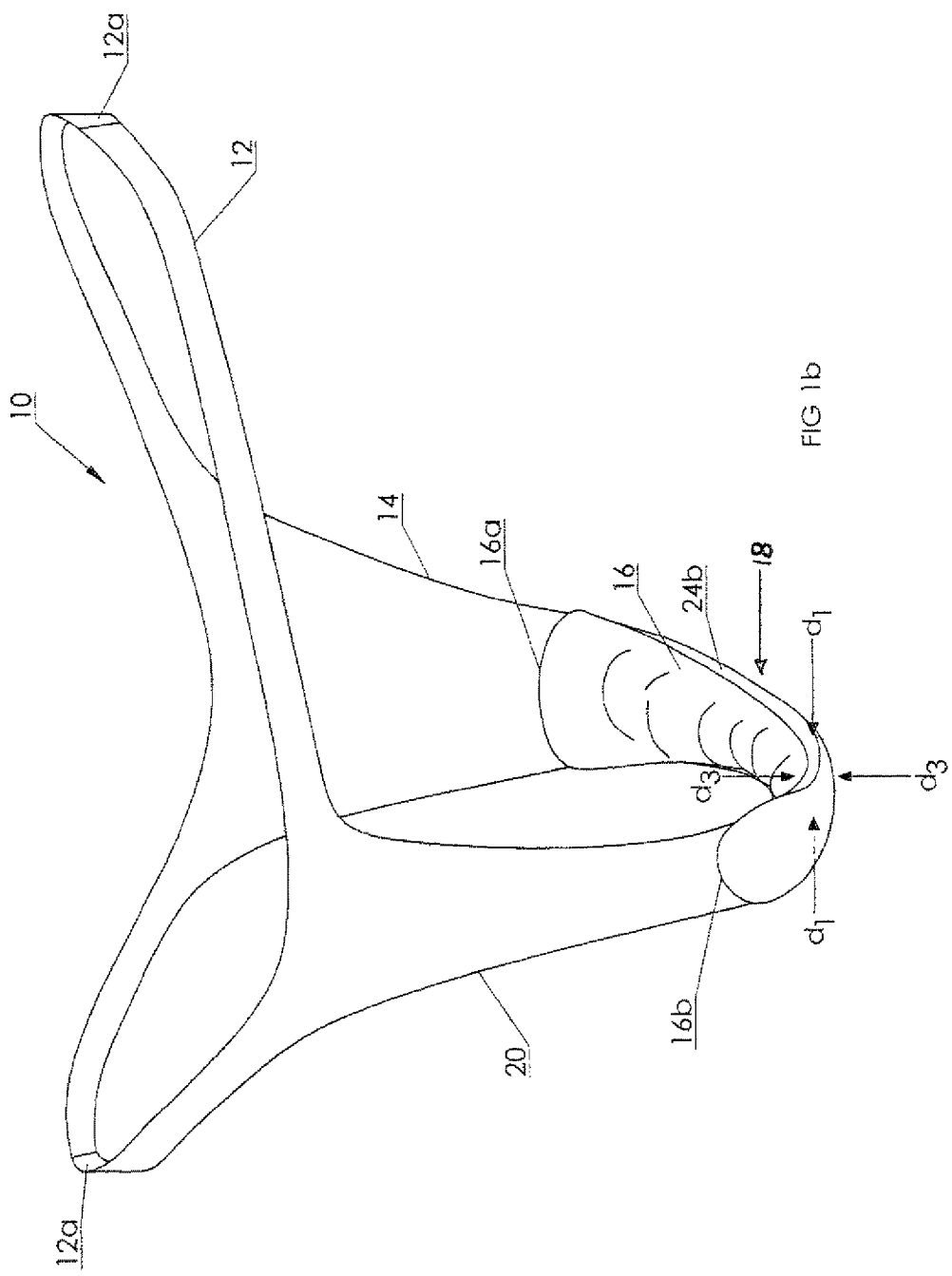
Figure 1C:
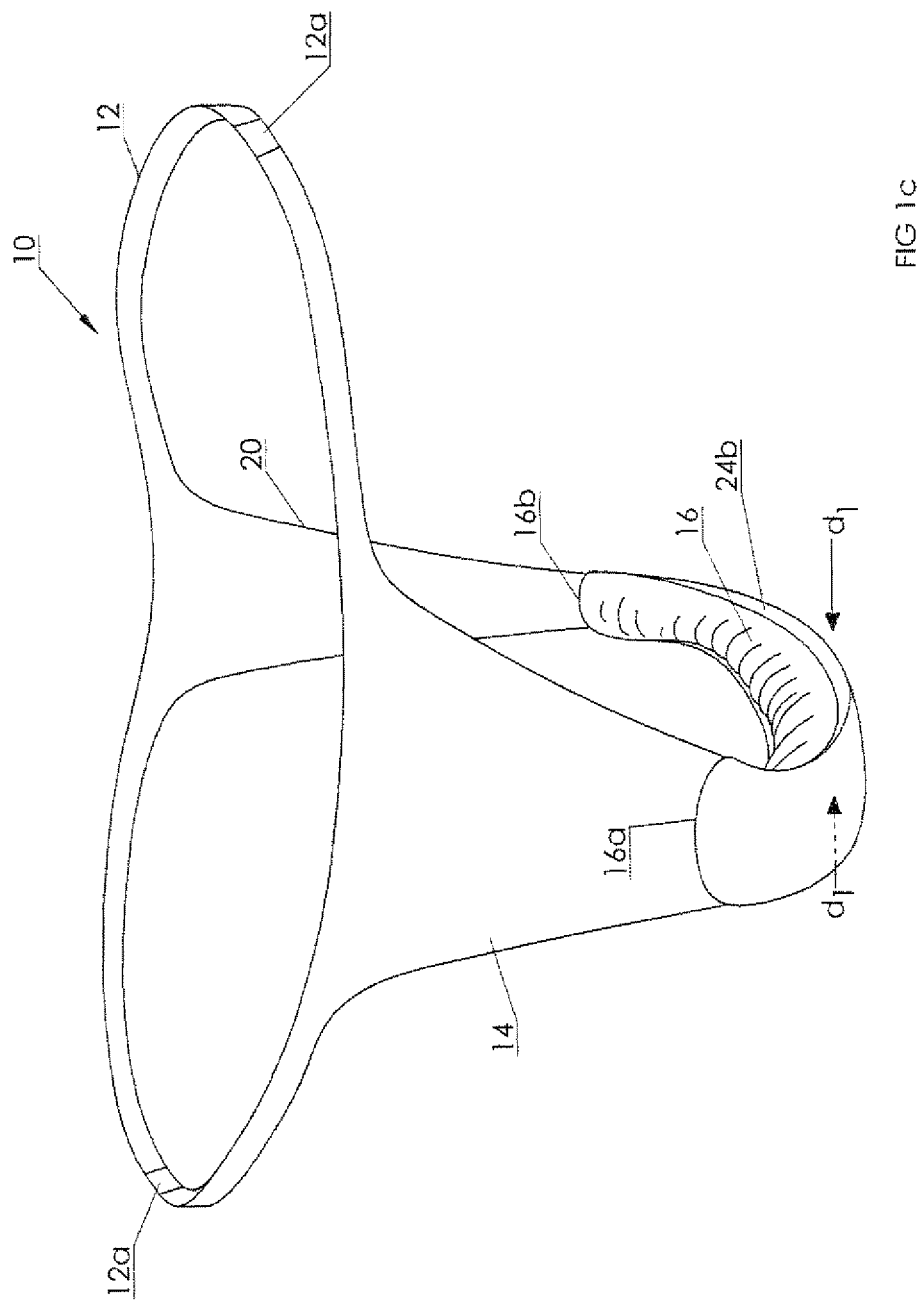
Figure 2A:
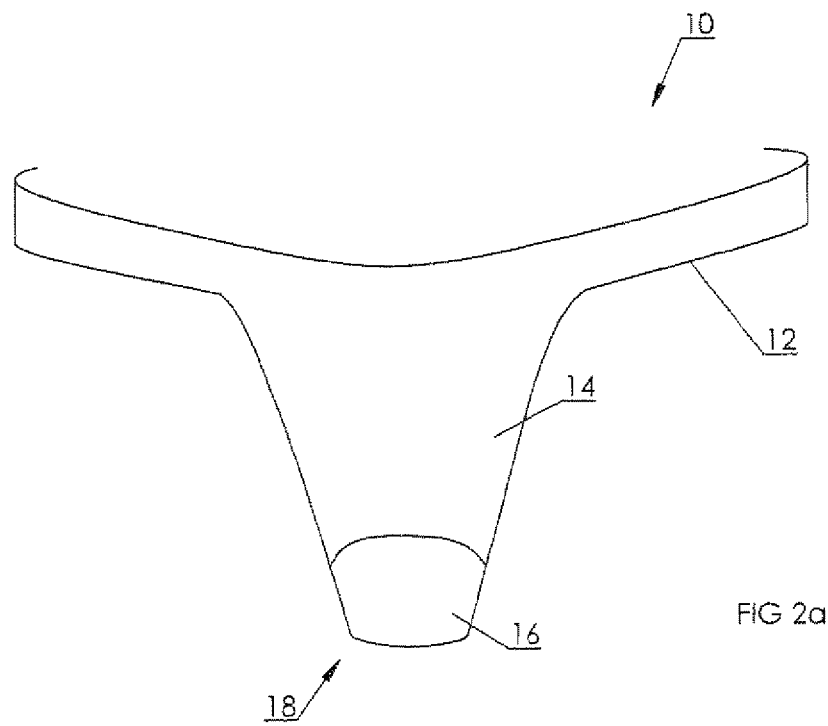
Figure 2B:
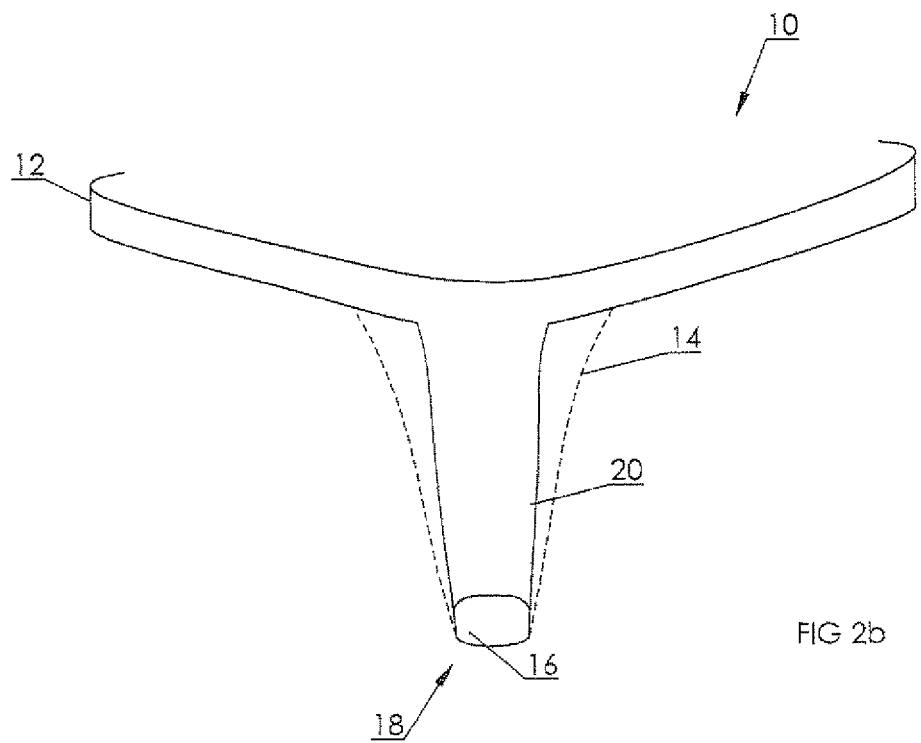
FIG. 2b is, in partially cut-away rear elevation view a thong supporting a pad according to the present invention.

In using conventional sanitary napkins, applicants had observed that often, even in heavy menstrual flow situations, not all of the available area of a conventional pad appeared to absorb flow. That is, parts of conventional pads remained unused and dry even during heavy flow days. Thus it appeared to the applicants that such designs were not efficient in that the wearer had to put up with wearing the extra bulk of the pad in places where the fluid was neither initially captured nor retained in. Thus in the development of the present invention the intention was to provide a flow capture channel for capturing the flow emitting from the vagina of the wearer and in particular raised channel walls to act as flow guides. Although applicants do not wish to be bound by a particular theory of operation, perhaps due to the walls being flat, that is smooth and generally vertically upstanding, or at least not overly corrugated or crenulated or puckered as would occur in the case of an elastic gathering of the side wall material to hold the side wall gathered for example around a leg opening such as in a diaper, applicants noticed that using the aforesaid channel design that the menstrual flow from the wearer migrated relatively quickly and noticeably quite far from the originating point of impact (initial entry area 30) of the flow onto the porous upper layer of the pad. Thus, even using flow rates in the mannequin testing which in applicants view likely exceeded human flow rates, and as noted above eventually exceeded normal human flow volumes for the flow of an entire menstrual cycle, the applicants noticed that the flow spread noticeably in directions B and C (as seen in FIG. 1a) substantially longitudinally away from the initial flow entry area 30. The flow was seen to migrate laterally from entry area 30 so as to show as a pair of coloured longitudinally extending bands 32 along the side walls. In applicants' observation, the flow in both directions B and C migrated a significant amount of the available longitudinal distance along the length of the pad, that is, a significant distance substantially parallel to longitudinal axis D of pad 16. Thus as more and more fluid was applied to pad 16 through upper layer 22a, the flow migrated from a mid-portion 34 corresponding to initial flow entry area 30 longitudinally forwardly in direction B to a forward reservoir portion 36a and rearwardly in direction C to a smaller reservoir portion 36b. It is applicants opinion that the flow migrated at a sufficient rate in directions B and C from the bulk of primary absorbent material 26 located underneath initial flow entry area 30 so that with a combination of the wicking of the flow in the cotton wool, and the guiding by beads 30c and the side walls 24a of the lateral spread of the flow into longitudinal directions noticeably along side walls 24a in directions E, that more and more fluid was able to be accommodated in mid-portion 34 by reason of the flow away from initial flow entry area 30 and into the reservoir portions 36a and 36b. It appeared to the applicants that the greatest fluid volume could be accommodated in the larger lateral width d4 of the forward portion of pad 16 than in the restricted volume under area 30. In applicants view, this takes advantage in the forward reservoir area of the increased lateral width of the material used in front v-shaped portion 14 in typical thong-style underwear. That is, a larger reservoir area may be accommodated behind the wider front panel of thong underwear, without increased thickness of the pad. Thus in applicants view, if the flow could be migrated at a sufficient rate into, for example, the forward reservoir portion 36a and away from the initial flow entry area 30, that, combined with control of the lateral flow and guiding the lateral flow into a longitudinal direction so as to guide the lateral flow towards a reservoir area of the pad, that leakage of the pad would be inhibited if not entirely prevented as the pad accommodated volume flow rates and volume amounts which might be expected during a normal menstrual flow if not a menstrual flow approaching menorrhagia. In this fashion, applicants expected and observed increased efficiency in the use of the sanitary pad material over that observed in conventional so-called maxi-pads.

It may also be that as a wearer of a thong-style pad according to the present invention walks or otherwise scissors their legs (as in a walking motion), that the pressing of the wearer's inner thighs (adjacent the perineum) against the outsides of the pair of side walls 24a, and combined with the scissoring motion of the inner thighs, that fluid within the pad and along the inside of the side walls is urged longitudinally forward and rearward in what may be a slight pumping action. That is, the thighs as they move translate along the side walls in the waist of the pad, slightly deformed or pushing in on the side walls as the thighs slide over the waist portion of the side walls. Applicants postulate that, although they do not wish to be held to any particular theory of operation, the flexing of the side walls in a rhythmic oppositely disposed pattern of deflection may act to further urge fluid out of the mid-portion 34 and into the reservoir portions of the pad.

As will be apparent to those skilled in the art in the light of the foregoing disclosure, many alterations and modifications are possible in the practice of this invention without departing from the spirit or scope thereof. Accordingly, the scope of the invention is to be construed in accordance with the substance defined by the following claims.

What is claimed is:

1. A thong-style sanitary pad comprising:
a flexible fluid impervious lower layer,
a single, unitary flexible, fluid absorbent core mounted on said lower layer,
a flexible, porous upper layer mounted atop said fluid absorbent core,
wherein said lower layer, when laid flat, having an elongate substantially planar fluid impervious base extending longitudinally between opposite front and rear ends thereof and extending laterally between opposite first and second side edges thereof, wherein said first and second side edges are substantially mirror images of each other and each said side edge of said first and second side edges has a concave outline in plan form between said front and rear ends so as to define a waist along a mid-portion of said base between forward and rearward portions of said base adjacent said front and rear ends of said base respectively,
said lower layer having substantially smooth side walls extending upwardly from said base along said first and second side edges corresponding to at least said mid-portion of said base,
wherein said upper layer has first and second side edges which are mounted to corresponding said first and second side edges of said lower layer, and front and rear ends which are mounted to corresponding said front and rear ends of said lower layer so as to encase said fluid absorbent core between said upper layer, said base and said side walls of said lower layer, and wherein said fluid absorbent core extends substantially from said front ends to said rear ends of said upper and lower layers, and extends continuously from said first side edges to said second side edges of said lower and upper layers,
wherein said waist has a lateral dimension which is sized to snugly fit in use of said pad, snugly under a perineum of the user and between the tops of the user's inner thighs whereby a user so wearing said pad will fit said waist between a saddle portion of a thong being worn by the user and the user's perineum,
wherein said sidewalls extend upwardly substantially orthogonally from said base,
and further comprising a longitudinally extending flexible pair of flow guiding rails mounted to an upper surface of said base, wherein each of said pair of flow guiding rails are adjacent a corresponding said sidewall, and wherein said fluid absorbent core extends over, so as to rest on, said flow guiding rails,
and wherein said flow guiding rails comprise adhesive having a height substantially in a range chosen from the group comprising: 0.5-3.5 millimeters, 5-10 percent of a height of said sidewalls.

2. The pad of claim 1 wherein said height of said rail is chosen from the group comprising: substantially 10 percent of a height of a corresponding sidewall of said sidewalls, 1-3 millimeters.

3. The pad of claim 1 wherein said rails are spaced apart from said side walls.

4. The pad of claim 1 further comprising a disposable thong portion for supporting said upper layer against the perineum and vulva of the user, and so as to position said mid-portion adjacent the vulva.

5. The pad of claim 1 further comprising a flexible lower cover layer having circumferential edges therearound mounted under said lower layer, said circumferential edges mounted to said edges of said upper layer along an upwardly oriented boundary seam, said seam extending along said sidewalls so as to support said sidewalls in said upward substantially orthogonal orientation relative to said base.

6. The pad of claim 1 wherein said pair of flow guiding rails are a pairs of resilient beads.

7. The pad of claim 1 wherein said pair of flow guiding rails is a pair of resilient strips.

8. The pad of claim 6 wherein said beads bond said core to said lower layer.

9. The pad of claim 1 wherein said pair of flow guiding rails form opposite sides of a continuous flexible ridge extending substantially continuously around, and inset from, a circumferential edge of said base.

10. The pad of claim 1 wherein said waist has a lateral dimension and a corresponding vertical dimension and wherein a ratio of said vertical dimension to said lateral dimension is substantially in the range of a ratio of ½:1 to a ratio of 1:1.

* * * * *